United States Patent
Podmore et al.

(10) Patent No.: US 9,549,795 B2
(45) Date of Patent: Jan. 24, 2017

(54) SALIVA MANAGEMENT SYSTEM WITH CONTINUOUS FLOW THROUGH ORAL DEVICE

(71) Applicant: APNICURE, INC., Redwood City, CA (US)

(72) Inventors: Jonathan Podmore, San Carlos, CA (US); Nicholas R. Vitale, Foster City, CA (US); John Edwards Crowe, Menlo Park, CA (US); Matthias Vaska, Palo Alto, CA (US)

(73) Assignee: ApniCure, Inc., Redwood City, CA (US)

( * ) Notice: Subject to any disclaimer, the term of this patent is extended or adjusted under 35 U.S.C. 154(b) by 67 days.

(21) Appl. No.: 14/624,088

(22) Filed: Feb. 17, 2015

(65) Prior Publication Data

US 2015/0157433 A1   Jun. 11, 2015

Related U.S. Application Data

(62) Division of application No. 13/023,763, filed on Feb. 9, 2011, now Pat. No. 8,979,823.

(51) Int. Cl.
*A61C 17/06* (2006.01)
*A61M 1/00* (2006.01)
(Continued)

(52) U.S. Cl.
CPC .............. *A61C 17/043* (2013.01); *A61F 5/566* (2013.01); *A61M 1/0023* (2013.01);
(Continued)

(58) Field of Classification Search
CPC .... A61C 17/043; A61F 5/566; A61M 1/0023; A61M 1/0025; A61M 1/0058; A61M 1/0084; A61M 16/0488; A61M 16/049; A61M 16/0493; A61M 16/0495; A61M 2210/0625; A61M 2210/0643
See application file for complete search history.

(56) References Cited

U.S. PATENT DOCUMENTS 2,560,915 A   7/1951  Bamberger
3,132,647 A   5/1964  Corniello
(Continued)

FOREIGN PATENT DOCUMENTS

EP   1862152 A1   12/2007
JP   2009502301 A   1/2009
(Continued)

OTHER PUBLICATIONS

Cartwright et al., "The effects of a non-surgical treatment for obstructive sleep apnea: the tongue retaining device;" JAMA, Aug. 1982; 248(6): 705-709.
(Continued)

*Primary Examiner* — Adam Marcetich
(74) *Attorney, Agent, or Firm* — Wilson, Sonsini, Goodrich & Rosati

(57) ABSTRACT

Systems for maintaining a vacuum in a patient's oral cavity comprises an oral device, a vacuum control system, and an assembly including first and second tubes for connecting the vacuum control system to the oral device. The oral device has an internal plenum, and a vacuum is drawn in the plenum by a vacuum pump connected by a first tube of the tubular assembly. The vacuum is maintained by an air source which is connected to the plenum by the second tube of the tubular assembly. By maintaining a constant circulating air bleed through the oral device and the connecting tubes, saliva may be removed from the system and collected in a saliva trap located before the vacuum pump.

7 Claims, 4 Drawing Sheets

(51) Int. Cl.
*A61M 16/04* (2006.01)
*A61F 5/56* (2006.01)
*A61C 17/02* (2006.01)

(52) U.S. Cl.
CPC ........ *A61M 1/0025* (2014.02); *A61M 1/0058* (2013.01); *A61M 1/0084* (2013.01); *A61M 16/049* (2014.02); *A61M 16/0488* (2013.01); *A61M 16/0493* (2014.02); *A61M 16/0495* (2014.02); *A61C 17/0211* (2013.01); *A61M 2210/065* (2013.01); *A61M 2210/0625* (2013.01); *A61M 2210/0643* (2013.01)

(56) References Cited

U.S. PATENT DOCUMENTS

| | | | |
|---|---|---|---|
| 3,566,869 A | 3/1971 | David | |
| 3,731,675 A * | 5/1973 | Kelly | A61C 17/0211 601/164 |
| 3,952,743 A | 4/1976 | Harrison | |
| 4,164,940 A | 8/1979 | Quinby | |
| 4,169,473 A | 10/1979 | Samelson | |
| 4,304,227 A | 12/1981 | Samelson | |
| 4,669,459 A | 6/1987 | Spiewak et al. | |
| 4,676,240 A | 6/1987 | Gardy | |
| 4,735,606 A | 4/1988 | Davison | |
| 5,018,967 A | 5/1991 | Schwalbach | |
| 5,034,006 A | 7/1991 | Hosoda et al. | |
| 5,050,616 A | 9/1991 | Wolff et al. | |
| 5,104,315 A | 4/1992 | McKinley | |
| 5,127,411 A | 7/1992 | Schoolman et al. | |
| 5,465,734 A | 11/1995 | Alvarez et al. | |
| 5,490,499 A * | 2/1996 | Heinonen | A61M 16/00 128/203.28 |
| 5,503,629 A | 4/1996 | Catone et al. | |
| 5,513,986 A | 5/1996 | Feltham et al. | |
| 5,588,836 A | 12/1996 | Landis et al. | |
| 5,738,656 A | 4/1998 | Wagner | |
| 5,915,385 A | 6/1999 | Hakimi | |
| 5,957,133 A | 9/1999 | Hart | |
| 5,989,193 A | 11/1999 | Sullivan | |
| 6,454,724 B1 | 9/2002 | Greene | |
| 6,494,209 B2 | 12/2002 | Kulick | |
| 6,679,257 B1 | 1/2004 | Robertson et al. | |
| 6,820,617 B2 | 11/2004 | Robertson et al. | |
| 6,877,513 B2 | 4/2005 | Scarberry et al. | |
| 6,955,172 B2 | 10/2005 | Nelson et al. | |
| 6,976,491 B2 | 12/2005 | D'Agosto | |
| 6,997,186 B2 | 2/2006 | Robertson et al. | |
| 7,073,505 B2 | 7/2006 | Nelson et al. | |
| 7,073,506 B2 | 7/2006 | Robertson et al. | |
| 7,182,082 B2 | 2/2007 | Hoffrichter | |
| 7,328,698 B2 | 2/2008 | Scarberry et al. | |
| 7,451,766 B2 | 11/2008 | Miller | |
| 7,509,164 B2 | 3/2009 | Jensen et al. | |
| 7,935,065 B2 | 5/2011 | Martin et al. | |
| 8,074,656 B2 | 12/2011 | Vaska et al. | |
| 8,701,672 B2 | 4/2014 | Vaska | |
| 8,979,823 B2 | 3/2015 | Podmore et al. | |
| 2001/0047805 A1 | 12/2001 | Scarberry et al. | |
| 2002/0082544 A1* | 6/2002 | Thrash | A61C 17/0211 604/28 |
| 2002/0104538 A1* | 8/2002 | Emtell | A61M 16/0081 128/205.14 |
| 2005/0037315 A1* | 2/2005 | Inoue | A61C 19/063 433/80 |
| 2005/0166928 A1 | 8/2005 | Jiang | |
| 2005/0166929 A1 | 8/2005 | Jiang | |
| 2005/0236003 A1 | 10/2005 | Meader | |
| 2006/0096600 A1 | 5/2006 | Witt et al. | |
| 2006/0282010 A1 | 12/2006 | Martin et al. | |
| 2007/0184404 A1 | 8/2007 | Johnki | |
| 2007/0277818 A1 | 12/2007 | Chen | |
| 2008/0092891 A1* | 4/2008 | Cewers | A61M 16/12 128/204.18 |
| 2008/0168989 A1* | 7/2008 | Cewers | A61M 16/20 128/204.21 |
| 2008/0188947 A1 | 8/2008 | Sanders | |
| 2008/0200877 A1 | 8/2008 | Panotopoulos | |
| 2008/0210244 A1 | 9/2008 | Keropian | |
| 2008/0216843 A1 | 9/2008 | Jiang | |
| 2008/0308112 A1 | 12/2008 | Aarts | |
| 2009/0120446 A1 | 5/2009 | Vaska et al. | |
| 2009/0120447 A1 | 5/2009 | Vaska et al. | |
| 2009/0123886 A1 | 5/2009 | Vaska | |
| 2009/0198201 A1 | 8/2009 | Adahan | |
| 2009/0208898 A1 | 8/2009 | Kaplan | |
| 2010/0043804 A1 | 2/2010 | Razmovski | |
| 2010/0113956 A1 | 5/2010 | Curti et al. | |
| 2010/0147302 A1 | 6/2010 | Selvarajan et al. | |
| 2010/0288288 A1* | 11/2010 | Hegde | A61F 5/566 128/848 |
| 2011/0027748 A1 | 2/2011 | Fusi, II et al. | |
| 2011/0220124 A1 | 9/2011 | Vaska et al. | |
| 2012/0132215 A1 | 5/2012 | Vaska et al. | |
| 2012/0132216 A1 | 5/2012 | Vaska | |
| 2012/0199135 A1 | 8/2012 | Podmore et al. | |

FOREIGN PATENT DOCUMENTS

| | | | |
|---|---|---|---|
| JP | 2011502715 A | | 1/2011 |
| WO | WO-2009064914 A1 | | 5/2009 |

OTHER PUBLICATIONS

Engelke et al., "Preliminary radiographic observations of the tongue-repositioning manoeuvre" Eur. J. of Orthodontics, 2006; 28: 618-623.
European search report dated Oct. 23, 2012 for EP Application No. 08849727.6.
Hoffstein, "Review of oral appliances for treatment of sleep-disordered breathing," Sleep Breath, 2007 Mani 1 (1):1-22.
International Search Report and Written Opinion dated Mar. 17, 2009 for PCT Application No. US2008/083440.
International search report and written opinion dated Jun. 12, 2012 for PCT/US2012/024030.
Notice of allowance dated Dec. 12, 2014 for U.S. Appl. No. 13/023,793.
Office action dated Mar. 12, 2013 for U.S. Appl.No. 13/368,182.
Office action dated Jun. 4, 2013 for U.S. Appl. No. 13/365,791.
Office action dated Jun. 23, 2014 for U.S. Appl. No. 13/023,793.
Office action dated Aug. 15, 2013 for U.S. Appl. No. 13/023,793.
Office action dated Aug. 19, 2011 for U.S. Appl. No. 12/269,683.
Office action dated Oct. 16, 2013 for U.S. Appl. No. 13/023,793.
Office action dated Dec. 3, 2013 for U.S. Appl. No. 13/368,182.
U.S. Appl. No. 12/840,076, filed Jul. 20, 2010.
U.S. Appl. No. 13/365,791, filed Feb. 3, 2012.
U.S. Appl. No. 13/368,182, filed Feb. 7, 2012.
U.S. Appl. No. 13/912,021, filed Jun. 6, 2013.
Notice of allowance dated Dec. 12, 2014 for U.S. Appl. No. 13/023,763.
Office action dated Jun. 23, 2014 for U.S. Appl. No. 13/023,763.
Office action dated Aug. 15, 2013 for U.S. Appl. No. 13/023,763.
Office action dated Oct. 10, 2014 for U.S. Appl. No. 13/023,763.
Office action dated Oct. 16, 2013 for U.S. Appl. No. 13/023,763.

* cited by examiner

SALIVA MANAGEMENT SYSTEM WITH CONTINUOUS FLOW THROUGH ORAL DEVICE

CROSS-REFERENCE

This application is a divisional application of Ser. No. 13/023,763, filed Feb. 9, 2011, which is incorporated herein by reference in its entirety, and to which application we claim priority under 35 USC §121.

BACKGROUND OF THE INVENTION

1. Field of the Invention

The present invention relates generally to medical devices and methods. In particular, the present invention relates to a system, device and method for managing saliva accumulation in an oral device that may be held in the mouth of a patient to reduce the incidence of obstructive sleep apnea or snoring or for other purposes.

Obstructive sleep apnea (OSA) is a serious medical condition resulting from a temporary airway blockage which occurs as a patient sleeps. The airway blockage usually occurs between the soft palate and/or the back of the tongue and the pharynx. As the patient breathes, the reduced area in the upper airway can cause snoring, and more seriously, OSA.

Sleep disruption caused by OSA can result in severe daytime sleepiness, chronic fatigue, headaches, depression, accidents, injuries, and of particular concern, OSA can reduce the amount of oxygen entering the lungs causing hypoxia. Hypoxia, in turn, can lead to pulmonary hypertension, heart disease, and stroke.

Numerous invasive and less invasive treatments have been proposed for OSA. Of particular interest to the present invention, "continuous positive airway pressure" (CPAP) delivers a continuous stream of pressurized air directly to the person's upper airway. The positive pressure maintains potency of the airway and inhibits the collapse associated with OSA. Although generally effective, CPAP suffers from a number of drawbacks that have led to a high level of non-compliance. The patient must wear a bulky facial mask which can be uncomfortable, and the system generates noise that can make falling asleep difficult. CPAP is also difficult to use because the mask requires careful fitting to avoid air leaks and facial discomfort and because the mask can easily be dislodged during sleep. Moreover, a number of unpleasant side effects, such as sore throats, dry throat and eyes, headaches, and skin rashes from the mask frequently occur. These problems have resulted in a high level of non-compliance with CPAP therapy.

As an improvement over CPAP, it has been proposed to apply a negative pressure to the patient's oral cavity. For example, devices have been proposed which apply a vacuum at the forward end of the patient's mouth, typically at or just behind the lips, to pull the tongue forward in order to lift the rear portion of the tongue away from the back of the airway. See, for example, U.S. Patent Publication Nos. 2007/0277818, 2005/0166928 and 2005/0166929. As an improvement over these devices, it has more recently been proposed to apply a negative pressure in region or space above the tongue which in turn draws the soft palate away from the pharynx to draw the rear portion of the tongue away from the pharynx as well. See, commonly owned U.S. Patent Publication Nos. 2009/0120446 and 2009/0120447.

With all such oral devices, saliva can accumulate in the vacuum lines and vacuum pump connected to the oral device. While it is proposed in commonly owned U.S. Patent Publication No. 2009/0123886 to collect saliva from the vacuum lines using a liquid trap in the connecting line between the oral device and the pump, the saliva can still collect in the connecting line and result in an unpredictable additional pressure drop between the pump and the oral device. To help clear the connecting line, it is further proposed to provide a positive pressure pump to introduce air to the oral cavity or to connect an air bleed line to the remote end of the vacuum line to allow a continuous air circulation. Even these measures, however, have not been entirely effective in removing saliva from the system to eliminate blockages and unpredictable pressure drops. In particular, saliva can still accumulate in the oral device itself which can increase the actual pressure drop in ways that are difficult to predict and address.

For these reasons, it would be desirable to provide alternative and improved methods and apparatus for drawing a vacuum in a patient's oral cavity for treating obstructive sleep apnea and other purposes. The methods and devices should be effective both in clearing saliva from the vacuum connecting line and in keeping the oral device free of accumulated saliva. The methods and systems should be simple and inexpensive to implement and add little or no complexity to the control system At least some of these objectives will be met by the inventions described below.

2. Description of the Background Art

Commonly owned U.S. Patent Publication Nos. 2009/0120446; 2009/0120447; and 2009/0123886, have been described above. Oral and external devices for treating sleep apnea and snoring are described in U.S. Patent Publication Nos. US2005/166929; US2005/166928; US2008/0188947; US2007/0277818; US2008/0216843; and US2008/0210244; and in U.S. Pat. Nos. 7,182,082; 7,073,506; 7,073,505; 6,955,172; 6,877,513; 6,494,209; 5,957,133; 5,465,734; 4,676,240; 4,304,227; 4,169,473; and 3,132,647; and in Cartwright and Samelson "The effects of a non-surgical treatment for obstructive sleep apnea: the tongue retaining device;" Journal of the American Medical Association 248 (1982).

SUMMARY OF THE INVENTION

The present invention provides systems, apparatus, and methods for inhibiting saliva accumulation in oral devices and systems which draw a vacuum in a patient's oral cavity for treating obstructive sleep apnea (OSA) or for other purposes. The present invention provides for a continuous air bleed circulation through all parts of the system where saliva might accumulate, particularly including the oral device and connecting line(s) between the oral device and a vacuum pump and optionally other system components. While other gases could be bled through the device, as a practical matter air will almost always be used.

The continuous air bleed circulation can be provided by making certain modifications to the systems described in the commonly-owned published patent applications above. First, the oral device is provided with a vacuum plenum having an inlet and an outlet, as well as vacuum port(s) which are disposed to draw vacuum in the patient's oral cavity. A vacuum pump is connected to the plenum outlet of the oral device, and an air source is coupled to the plenum inlet of the oral device. The vacuum pump is operated to draw a vacuum in the vacuum plenum while a small, controlled air bleed (typically in the range from 60 ml/min to 120 ml/min) results from the air entering the plenum from the air source. This continuous air bleed circulation will occur even when the vacuum ports in the vacuum plenum are receiving no air from the oral cavity. In prior devices, when the vacuum ports were blocked, the saliva could remain stagnant within the oral device and/or the connecting lines thus compromising operation of the system.

The plenum within the oral device may have any one of a variety of flow patterns. Most commonly, the plenum will extend from an inlet located at an anterior end of the device, through a first bite structure or leg of the device, across a cross-member at a posterior end of the device, and return through a second bite structure or leg of the device to the outlet. In other configurations, however, the plenum within the oral device need not be continuous. For example, the plenum could extend from the inlet up through the first bite structure or leg and terminate at a bypass outlet near a posterior end of the device. A second segment of the plenum, typically isolated from the first plenum segment, would have the vacuum ports and provide a return path to the device outlet, typically through the second bite structure or leg. The desired continuous air bleed circulation would thus pass through patient's oral cavity, where the air bleed would exit into the oral cavity through the bypass port and return into the second segment of the plenum through the vacuum port(s) on the posterior end of the device. In still another embodiment, plenum inlet and outlet segments can be formed in a single bite structure or leg of the device by providing a dividing wall in an interior luminal passage of the bite structure or leg. Thus, air can enter an inlet side of the plenum through the device inlet, flow to the vacuum port(s) on the posterior side of the device, and return to the outlet through an isolated passage formed on the other side of the dividing wall. A variety of other structures may also be possible so long as those structures provide for the continuous bleed of air through all air passages of the oral device including those within the region adjacent to the vacuum port(s) on the posterior end of the device.

In a first aspect of the present invention, a system comprises an oral device and a vacuum control system. The oral device is positionable in a patient's oral cavity (i.e., an interior portion of the mouth) and has a vacuum plenum with an outlet, an inlet, and one or more vacuum ports, typically located between the outlet and the inlet. The vacuum control system includes a vacuum pump, an air source and optionally a saliva trap or other removal mechanism. The vacuum control system is connected to the oral device by first and second tubes, where the tubes may be separate or integrated into a common connector assembly. The first tube connects the inlet of the oral device to the air source of the vacuum control system and the second tube connects the outlet of the oral device to the vacuum pump. The saliva trap, if present, is typically disposed between the outlet of the oral device and the vacuum pump of the vacuum control system, although it could be located after the pump. The "trap" could be any removal mechanism such as a separator, an evaporator, or any other component which removes, evaporates, or collects the saliva.

The oral device of the system will usually comprise a base adapted to be held between a patient's upper and lower teeth, where the base has an anterior end, a posterior end, and a cross-member extending across the posterior end of the device. The plenum usually extends around the base and the vacuum ports are typically disposed on the cross-member while the plenum inlet and plenum outlet are disposed on an anterior end of the device. Optionally, for the treatment of OSA, the cross-member may be adapted to engage and depress an engagement region of the tongue to allow a tongue region anterior to the cross-member to rise relative to a posterior region of the tongue, as described in more detail in the commonly-owned publications cited above.

At least the vacuum pump, the air source, and the saliva trap of the vacuum control system will usually be contained or enclosed within a common enclosure, typically a tabletop box. Optionally the system may include sensors, such as pressure or flow sensors, to monitor the pressure or flow of the air bleed into the device and the pressure and/or flow of air being drawn from the device by the vacuum pump. Conveniently, such sensors may also be provided within the common enclosure. Such pressure and/or flow sensors allow the system operation to be monitored and can alert the user should the pressures and/or flows be operating outside of their expected ranges. For example, a difference between the air bleed pressure going into the oral device and the vacuum pressure being drawn out of the oral device by the vacuum pump could signal a blockage or other malfunction within the oral device.

In a second aspect, the present invention provides an oral device comprising a base adapted to be held between a patient's upper teeth and lower teeth. The base has an anterior end, a posterior end, and a cross-member extending across the posterior end. A plenum extends within the base from an inlet on the anterior end, through the cross-member, and to an outlet on the anterior end. The inlet and the outlet are connected by the plenum so that air entering the inlet flows through the cross-member before exiting the outlet. The oral device will further include at least one vacuum port, typically a plurality of vacuum ports formed in a wall of the cross-member in order to draw vacuum within the patient's oral cavity when the oral device is held therein.

The base of the oral device will typically include left and right bite structures, where the cross-member is disposed between the bite structures at their respective posterior ends. The cross-member of the device will typically be spaced inferiorly of (below) the hard palate when the base is held between the patient's teeth. The cross-member is thus able to provide a clear region free from structure between the cross-member and the hard palate and extending to the patient's soft palate. The at least one vacuum port is typically disposed on a superior (upper) surface of the cross-member, and the device may further comprise a lip seal coupled to the base and/or the vacuum tubes to inhibit air from entering the oral cavity through the mouth while the vacuum is being applied. In the exemplary embodiments, the cross-member comprises an arcuate rear edge and a curved superior surface. While the left and right bite structures and cross-member have been described separately, in some embodiments they will be formed as a single integrated structure as shown in the drawings.

In a third aspect, the present invention provides a method for drawing a vacuum in a patient's oral cavity. The method comprises placing an oral device in the patient's oral cavity, where the device has an inlet, an outlet, a plenum there between, and at least one vacuum port in a posterior region of the plenum. A vacuum is drawn on the plenum outlet of the oral device while the device is in the patient's oral cavity in order to establish an air flow into the plenum inlet, through the plenum and out from the outlet. The air flow into the inlet is typically controlled or restricted to maintain a controlled vacuum in the plenum, where at least one of (1) drawing the vacuum and (2) restricting or controlling the air flow into the inlet to maintain a vacuum in the plenum in the range from 20 mmHg to 75 mmHg. In this way, saliva and moist air which are drawn into the plenum from the patient's oral cavity may be trapped or otherwise removed, typically using a moisture trap, filter or evaporator, after the air is withdrawn from the outlet of the oral device.

Restricting or controlling the air flow will typically comprise placing a fixed orifice before the device inlet. In the simplest cases, the orifice could be within the inlet itself, but having the inlet open with the orifice risks the inlet getting blocked while the patient sleeps, either from debris or from the patient turning to block the inlet orifice in the pillow or other bedding. Usually, it is preferable that the fixed orifice be disposed within the common enclosure of the control system where it can be protected, thus minimizing the chance of accidental blockage. Alternatively, the air inlet flow and/or pressure could be controlled using a pump or other active system.

The vacuum is typically controlled by controlling the vacuum pump connected to the device outlet. Moisture is trapped (separated or evaporated from the air flow) in a moisture (saliva) trap or similar structure placed in a flow path downstream of the plenum outlet. Optionally, pressure or flow rate may be measured between the plenum inlet and the plenum outlet. Proper operation of the system can then be monitored by comparing the measured inlet flow/pressure and the outlet flow/pressure to confirm that they are within expected ranges.

DETAILED DESCRIPTION OF THE INVENTION

Figure 1:
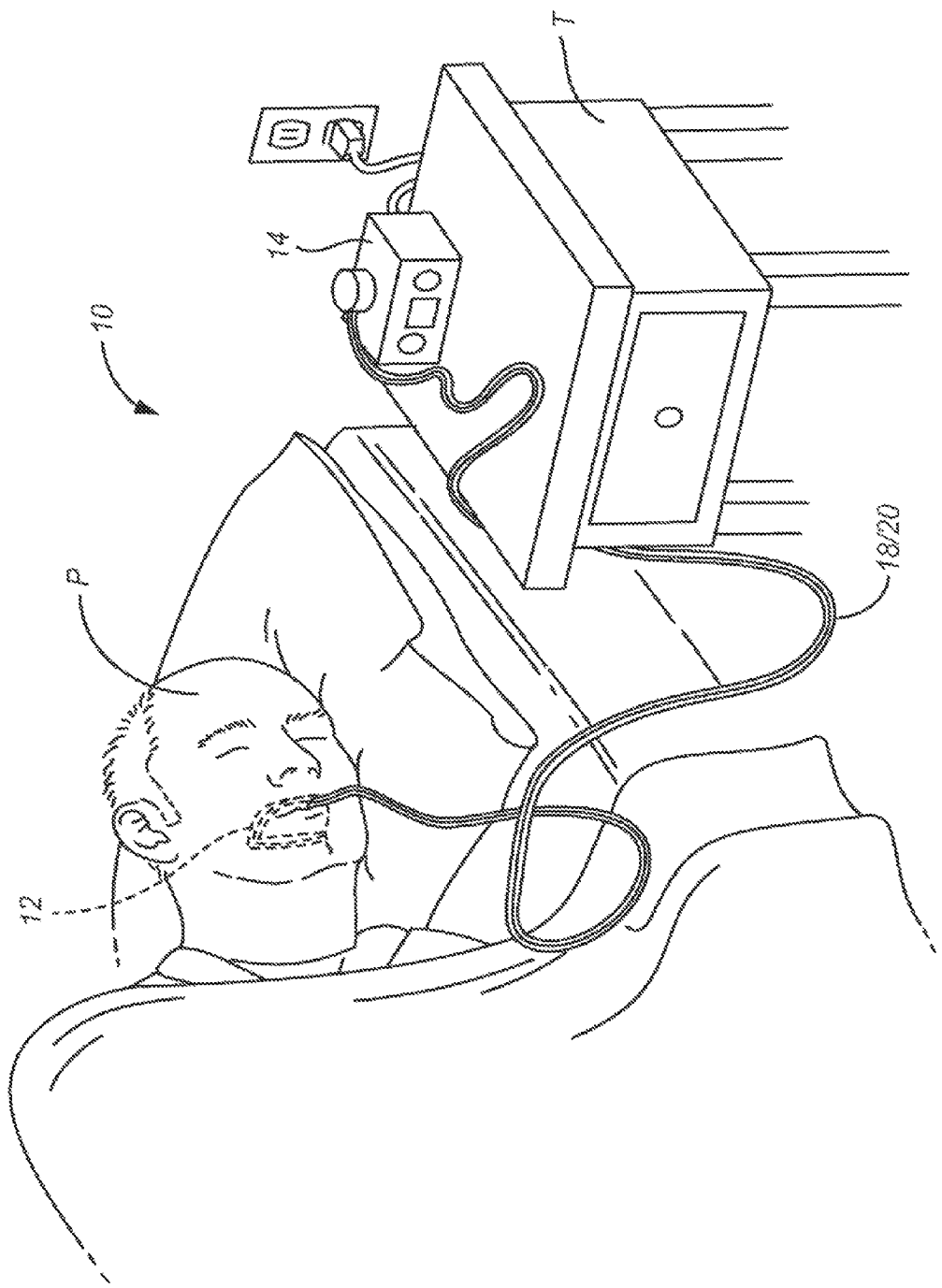
FIG. 1 illustrates a system constructed in accordance with the principles of the present invention in use by a patient.

Referring to FIG. 1, a system 10 constructed in accordance with the principles of the present invention includes an oral device 12 (shown in broken line in the oral cavity of a patient P), a control enclosure 14 which is suitable for placement on the top of the table T, and a connector line assembly usually including first and second tubular connectors 18 and 20, better illustrated in FIG. 2-6.

Figure 2:
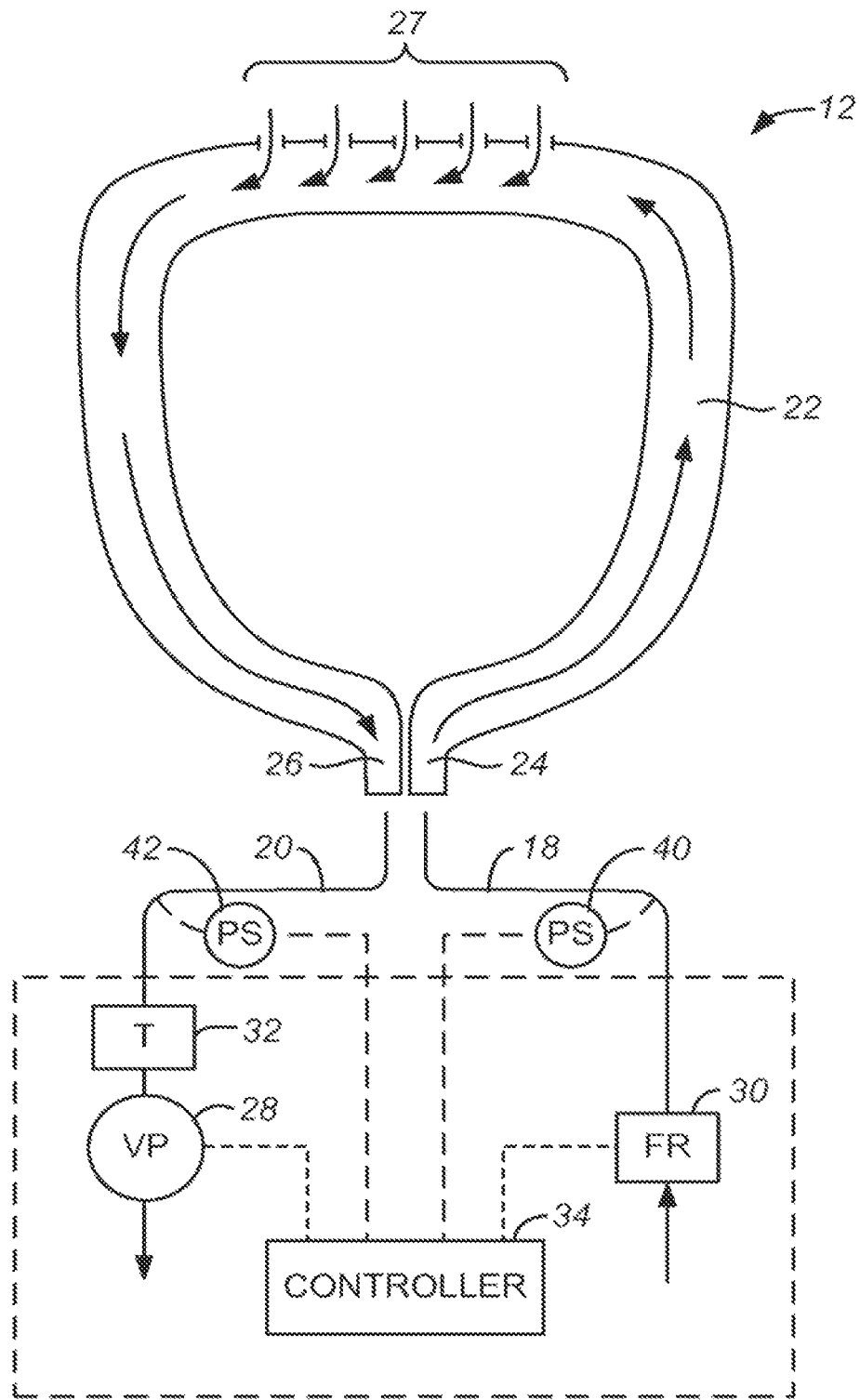
FIG. 2 is a schematic illustration of an oral device in combination with a vacuum control system in accordance with the principles of the present invention.

Referring now to FIG. 2, the oral device 12 includes an internal plenum 22 which extends from an inlet 24 to an outlet 26. The plenum 22 is typically integrally formed within the oral device 12, usually being formed as part of a molding process. Alternatively, the plenum 22 could be formed separately and attached to a separate body of the device. In addition to the inlet 24 and outlet 26, the oral device will include one or more vacuum ports 27, where the inlet s are typically formed on an anterior end of the device which will be held near the patient's lips in the oral cavity while the vacuums 27 are on the posterior end of the device which will be near the patient's soft palate when the device is in the patient's oral cavity.

A vacuum is drawn in the plenum 22 by vacuum pump 28 which is connected to the outlet 26 by tubular connector 20. To maintain a controlled vacuum in the plenum 22, an air source 30 is placed in front of the inlet 24, typically being connected by tubular connector 18. The vacuum pump 28 will typically be a diaphragm or other positive displacement pump where the pump speed may be varied in order to control the volume and/or pressure of air pulled from the device 12. In order to control the pressure, the delivery capacity of the air source 30 may be selected and/or controlled. Typically, the air source 30 will comprise a flow restrictor having a fixed orifice, more usually having an orifice area in the range from 0.01 mm$^2$ to 0.025 mm$^2$. Optionally, however, the air source 30 could comprise an adjustable orifice valve or a pump which is operated to deliver a fixed volume of air bleed into the plenum 22. In such cases, the controller could automatically control either the valve or the positive pressure pump to help maintain the target vacuum within the plenum of the oral device.

A saliva or moisture trap 32 will be placed in the flow path from the outlet 26 of the oral device 12 to the vacuum pump 28 in order to receive most or all of the air flow from the oral device and to remove saliva and moisture from the air flow before entering the vacuum pump. Usually, the trap 32 will be placed close to the inlet to the vacuum pump although it could be elsewhere in the system.

Usually, at least one pressure and/or flow sensor 40 will be provided in the air bleed inlet flow path between the air source 30 and the inlet 24, or optionally though less desirably within the plenum 22 of the device itself. The pressure/flow sensor 40 will detect the pressure/flow within the plenum either directly or indirectly, allowing controller 34 to control either the vacuum pump 28 and/or the air source 30 in order to maintain a target vacuum within the plenum, typically in the range from 20 mmHg to 75 mmHg, preferably in the range from 30 mmHg to 55 mmHg.

Optionally, a second pressure and/or flow sensor 42 may be provided between the outlet 26 of the oral device 12 and the vacuum pump 28, typically between the saliva trap 32 and the vacuum pump 28. The pressure and/or flow measured by sensor 42 can be compared with the reading from sensor 40 to make sure that the flow and/or pressure within the plenum 22 of the oral device 12 are within proper operating ranges. For example, should saliva or any other material or failure block flow within the plenum 22, the readings between the sensor 40 and sensor 42 would be expected to deviate substantially, indicating a system failure.

Figure 3:
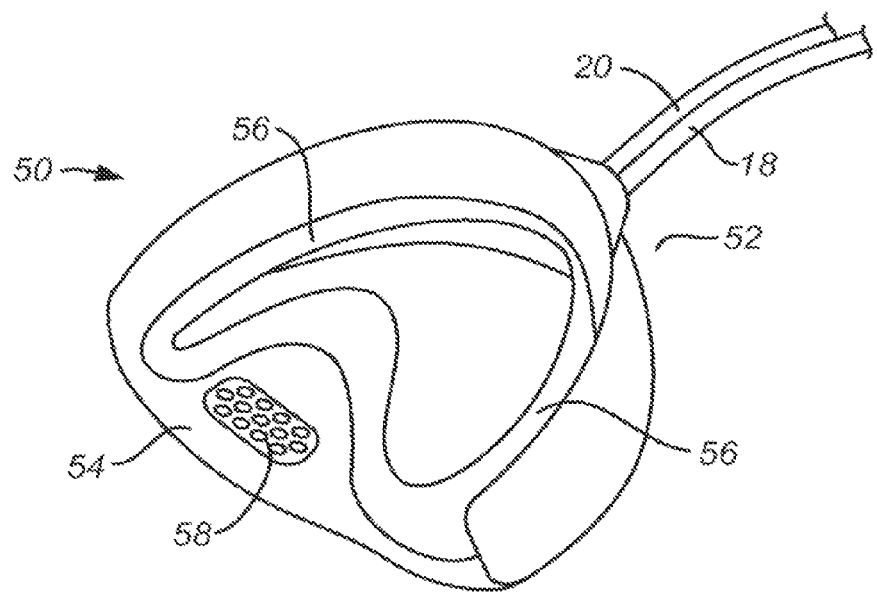
FIG. 3 is a perspective view of an oral device useful in the systems of the present invention.
Figure 4:
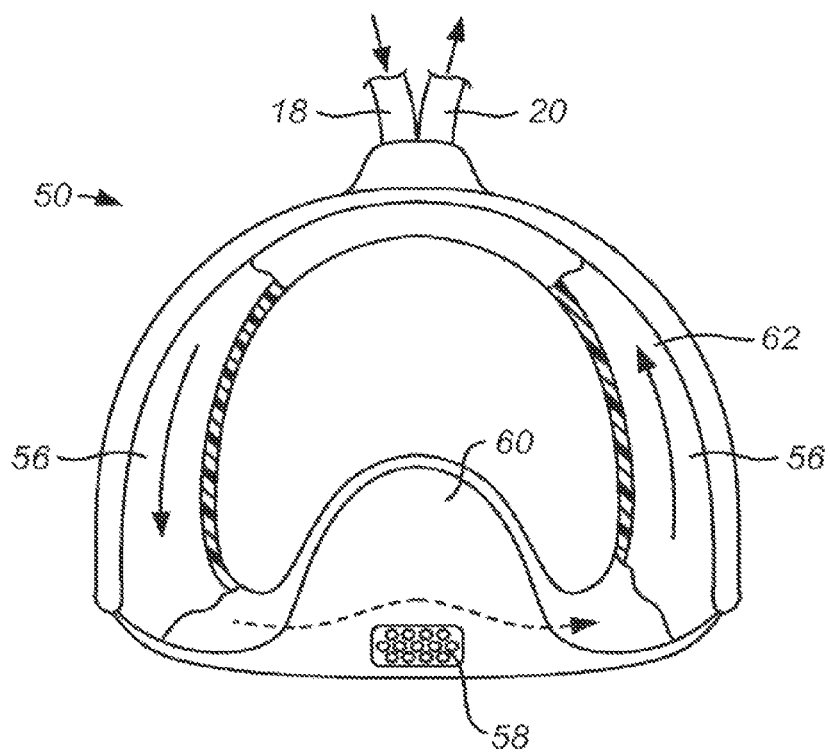
FIG. 4 is a partial cross-sectional view of the oral device of FIG. 3.

Referring now to FIGS. 3 and 4, an exemplary oral device 50 is illustrated. The oral device is fabricated from a polymer such as a polycarbonate or a polyvinyl acetate polymer (e.g., Versaflex® polymer), which may be molded or otherwise formed to have an anterior end 52 and a cross-member 54 at a posterior end. Bite plates 56 are formed on each side of the oral device 50, and the cross-member 54 includes a plurality of vacuum ports 58 formed on an upwardly and forwardly inclined surface 60 of the cross-member 54. Plenum 62 is formed in the interior of the oral device 50 and provides a circulation path shown by the arrows in FIG. 4. While the oral device 50 is exemplary of those useful in the systems and methods of the present invention, many other devices having the vacuum plenum, inlet and outlet, and vacuum ports would also be useful.

Figure 5:
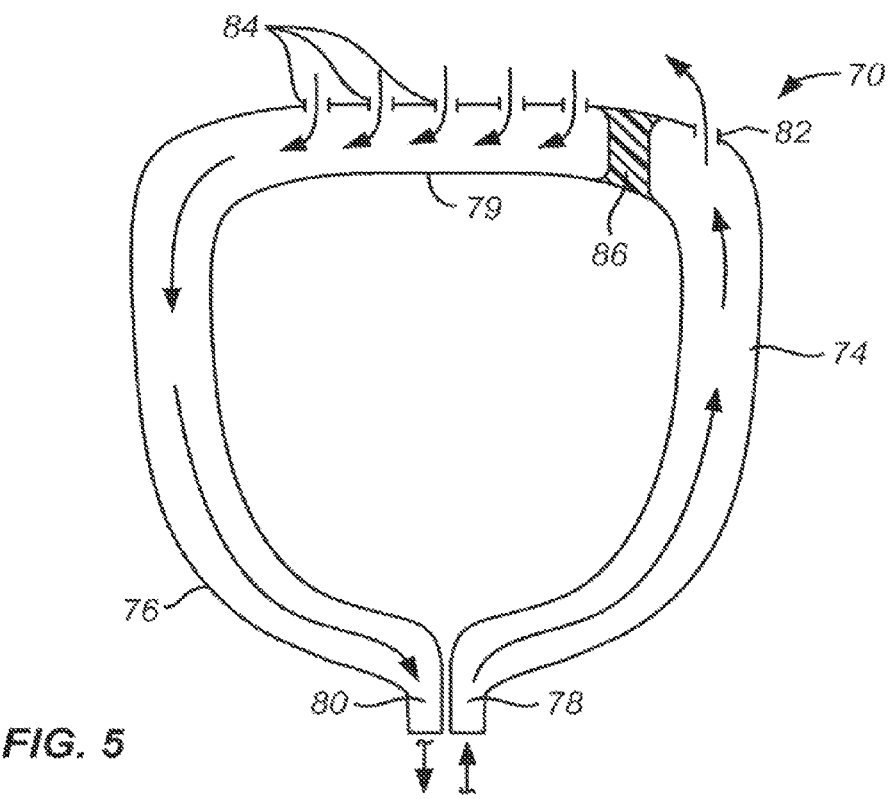
FIG. 5 is a schematic illustration of an alternative embodiment of the oral device of the present invention, said embodiment having a bypass port for passing the air bleed stream through the patient's oral cavity.

Referring to FIG. 5, an oral appliance 70 constructed in accordance with an alternative aspect of the present invention comprises a first bite structure or leg 74 and a second bite structure or leg 76. The first and second bite structures are joined at a posterior end by a cross-member 79 having a plurality of vacuum ports 84 formed over a posterior surface thereof. An air bleed, as generally described above, enters an interior passage or a lumen within the first bite structure 74 through an inlet 78. Instead of circulating through a continuous plenum to outlet 80, as with previous embodiments, the air entering through inlet 78 will pass into the patient's oral cavity through a bypass outlet 82. That air, or at least an equivalent volume or mass of air, will pass back into the plenum through the vacuum ports 84 together with any additional air which may have leaked into the patient's oral cavity which needs to be removed. The combined air streams will then flow down through the second bite structure or leg 76 and out the outlet 80, to the vacuum control system as described previously for other embodiments. In order to isolate the higher pressure region of the plenum in the first leg 74 from the lower pressure region of the plenum in the second leg 76, a barrier 86 will usually be disposed in the plenum between the bypass port 80 and the vacuum ports 84.

Figure 6:
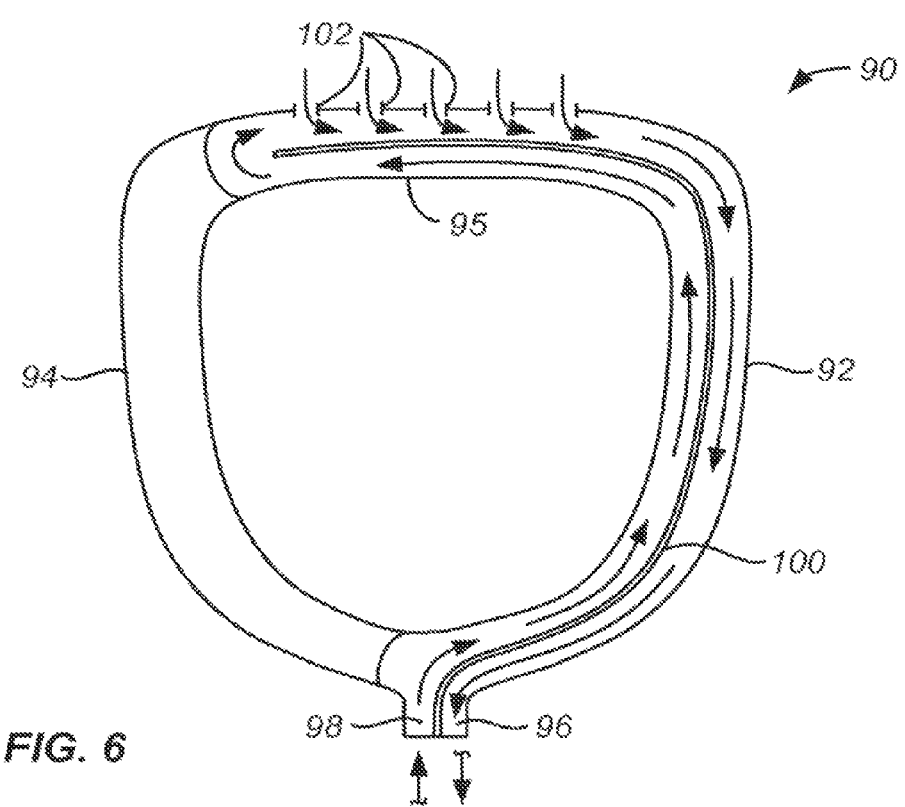
FIG. 6 is a schematic illustration of a further alternative embodiment of the oral device of the present invention showing air bleed inlet and outlet paths through a single bite structure or leg of the device.

Referring now to FIG. 6, an oral appliance 90 incorporating still alternative features of the present invention includes a first bite structure or leg 92 and a second bite structure or leg 94. The first bite structure 92 has an interior passage or lumen which is divided into inlet and outlet segments by a barrier or wall 100. A plenum inlet 98 is located at the anterior end of a first of the divided passages so that air bleed entering the inlet can flow in a posterior direction until it reaches cross-member 95 disposed between the bite structures 92 and 94. A wall or partition 100 terminates at that point so the air inflow can turn to pass in the opposite direction through the second portion of the divided air plenum so that a continuous air bleed is constantly maintained by vacuum port(s) 102 located on a posterior surface of the cross-member. The combined flows of the air bleed and any air which is drawn in through the vacuum port(s) then extends in an anterior direction through the other segment of the passage within the first bite structure so that it can exit through outlet 96. Usually, but not necessarily, the interior of the second bite structure or leg 94 will be blocked and isolated from the air flow so that it does not become contaminated.

While the above is a complete description of the preferred embodiments of the invention, various alternatives, modifications, substitutions, and equivalents may be used. Therefore, the above description should not be taken as limiting the scope of the invention, which is defined by the appended claims.

What is claimed is:

1. A method for drawing a vacuum in a patient's oral cavity, said method comprising:
   placing an oral device in the patient's oral cavity, said device having an inlet, an outlet, a plenum there between, and at least one vacuum port on a posterior region of the plenum;
   drawing a vacuum on the outlet to establish air flow into the inlet, through the plenum, and out from the outlet;
   restricting the airflow into the inlet to draw a vacuum in the plenum; and
   wherein at least one of the drawing of the vacuum and the restricting of the airflow into the inlet is controlled to maintain a vacuum wherein moist air will be drawn into the plenum from the patient's oral cavity.

2. A method as in claim 1, wherein the vacuum is maintained in the range from 20 mmHg to 70 mmHg.

3. A method as in claim 1, further comprising removing moisture from the air drawn by the vacuum.

4. A method as in claim 3, wherein moisture is trapped in a trap placed between the device output and the vacuum pump.

5. A method as in claim 1, wherein restricting comprises placing a fixed orifice before the device inlet.

6. A method as in claim 1, wherein the vacuum is controlled by controlling a vacuum pump connected to the device output.

7. A method as in claim 1, further comprising measuring pressures or flow of gas between a first point on the inlet and a second point on the outlet and comparing the measured pressures or flow of gas to determine if the system is functioning properly.

* * * * *